(12) United States Patent
Puppels (10) Patent No.: US 7,110,108 B2
(45) Date of Patent: Sep. 19, 2006

(54) SPECTROMETER FOR MEASURING INELASTICALLY SCATTERED LIGHT

(75) Inventor: Gerwin Jan Puppels, Rotterdam (NL)

(73) Assignee: River Diagnostics B.V., Rotterdam (NL)

( * ) Notice: Subject to any disclaimer, the term of this patent is extended or adjusted under 35 U.S.C. 154(b) by 0 days.

(21) Appl. No.: 10/480,479

(22) PCT Filed: Jun. 12, 2002

(86) PCT No.: PCT/NL02/00386

§ 371 (c)(1),
(2), (4) Date: Aug. 17, 2004

(87) PCT Pub. No.: WO02/101365

PCT Pub. Date: Dec. 19, 2002

(65) Prior Publication Data

US 2004/0263842 A1 Dec. 30, 2004

(51) Int. Cl.
*G01J 3/44* (2006.01)
(52) U.S. Cl. ........................ 356/301
(58) Field of Classification Search ........ 356/301
See application file for complete search history.

(56) References Cited

U.S. PATENT DOCUMENTS 2,940,355 A * 6/1960 Cary .................... 356/301
3,556,659 A * 1/1971 Hawes .................. 356/301
4,781,458 A * 11/1988 Angel et al. ............ 356/301
5,546,493 A   8/1996 Noguchi et al.
5,878,178 A * 3/1999 Wach ..................... 385/55
6,104,485 A * 8/2000 Wang et al. ............ 356/246
6,370,406 B1 * 4/2002 Wach et al. ............ 600/310

FOREIGN PATENT DOCUMENTS

EP        1462712 A1 * 9/2004
JP    2004294099 A  * 10/2004

* cited by examiner

*Primary Examiner*—Gregory J. Toatley, Jr.
*Assistant Examiner*—Isiaka O. Akanbi
(74) *Attorney, Agent, or Firm*—Hoffman & Baron, LLP (57) ABSTRACT

The spectrum of light, inelastically scattered by a sample (16) is measured. The light is guided through a capillary (12) from and to the sample, at least in one of these directions, through the channel no inelastic scattering of light occurs which can form an interfering background when measuring on the sample. By guiding the light through the channel, inelastic scattering of this light is prevented and it becomes possible to guide scattered light back through the channel to spectral analysis equipment (14) without problems with inelastic scattering during the guidance of the light. Preferably, the light is guided through the channel of the capillary in both directions.

22 Claims, 10 Drawing Sheets

SPECTROMETER FOR MEASURING INELASTICALLY SCATTERED LIGHT

This application is the U.S. National Phase of International Application Number PCT/NL02/00386 filed on 12 Jun. 2002, which is incorporated herein by reference.

BACKGROUND OF THE INVENTION

The invention relates to a spectrometer for measuring inelastically scattered light. Raman spectrometers are an example of spectrometers for measuring inelastically scattered light. When a sample is irradiated with monochromatic light, the light scattered by the sample will contain wavelength components different from those present in the incident light. So-called Raman scattering of light on molecules present in the sample creates this effect. With a Raman spectrometer, a sample is illuminated with a strong, essentially monochromatic light source. The light which is scattered by the sample is collected and the spectral distribution is analysed for spectral components with a wavelength different from that of the light source.

U.S. Pat. No. 5,862,272 describes the use of optic fibres for guiding Raman spectra of samples to and from the sample, while the sample is at a distance from the light source which is used for excitation and/or at a distance from the equipment for detection of the Raman signal. The use of optic fibres enables measurements at locations which are otherwise difficult to reach or cannot be reached at all, as is the case, for instance, in in vivo measurements on tissue, for instance in blood vessel examination or more generally in endoscopic applications, or as is the case in industrial applications such as in-line process control.

U.S. Pat. No. 5,862,273 describes the use of a filter at the extremity of the fibre (excitation-fibre) which guides the monochromatic light from the light source to the sample, adjacent the sample to be examined. This filter (excitation filter) only transmits light of the wavelength of the light source and no Rams scattered light from the fibre, which is generated therein by inelastic scattering of light from the monochromatic light source. This enables sensitive measurement, without interference by inelastically scattered light from the fibre which returns to the analysis unit after scattering or reflection on the sample.

Further, the use of an excitation filter in or an the excitation fibre necessitates the use of a different fibre or fibres (collection fibres) for collecting light scattered by the sample and its guidance to the analysis unit, since otherwise the Raman scattered light of interest would be stopped by the excitation filter so that it cannot reach the analysis unit. Special measures are necessary to obtain a good overlap between the volume or surface of the sample irradiated by light from the excitation fibre and the volume or surface of the sample from which scattered light is intercepted by the collection-fibre(s). Also, the use of separate fibres for supply of light to and discharge of light from the sample renders Raman probes complex. The signal collection efficiency is suboptimal and far-reaching miniaturisation is impeded.

The light scattered by the sample largely consists of elastically scattered light, having the same wavelength as the incident light from the monochromatic light source. This elastically scattered light of considerable intensity can tin give rise to the generation of Raman signal in the collection fibres, which leads to an interfering signal background. For that reason, for sensitive measurements, a filter (emission filter) is utilized before, on or in the collection fibre(s) on the side where the sample is located, which serves to stop the light scattered elastically by the sample and to transmit only the scattered light which is shifted in wavelength with respect to the wavelength of the monochromatic light source.

Using excitation and emission filters limits the use of the spectrometer to a light source of a particular wavelength and/or measurement of the Raman signal in a particular wavelength range. The necessity of the use of optic filters before, in or on the fibres close to the sample renders fibre optic probes for Raman spectroscopy complex.

Also from U.S. Pat. No. 6,208,887, a Raman spectroscope is known. This patent discusses the possibility of using a multimode laser. The sample is illuminated via an optical fibre, without the use of optic filters, so that the spectrometer is only suitable for low sensitivities. For receiving scattered light the possibility of any light guide (waveguide) is mentioned, without, however, mentioning the advantages thereof over optic fibres.

It is one object of the invention to provide a spectrometer for inelastic scattering with a simplified construction of the probe.

It is another object of the invention to provide such a spectrometer wherein further-reaching miniaturisation of the probe is possible.

It is a further object of the invention, among still further objects, to provide such a spectrometer which is designed such that sensitive measurements are possible, while no filters are required or fewer filters than in the prior art.

SUMMARY OF THE INVENTION

The spectrometer according to the invention is described in claim 1. This spectrometer utilizes a probe with a capillary with a channel through which at least one of the light transports of the light from the light source and the light scattered by the sample is guided. The other light transport can take place through the same channel or through a wall of the capillary if it is made of transparent material. Within the context of this invention, a capillary is understood to mean a flexible or non-flexible tube or pipe of any material (materials), with one or more channels in the longitudinal direction of the tube or pipe, which may be evacuated or filled with a gas (gasses) or a liquid (liquids).

Due to this construction, the probe is very compact. One capillary can suffice for guiding light to and from the sample. The location where the light leaves the capillary to illuminate the sample and the location where the light returns scattered from the sample into the capillary are in each other's immediate vicinity. No complex constructions are required for creating an overlap between the area of the sample which is irradiated and the area from which light returns to the analysis unit. Moreover, for the light transport through the channel in sensitive measurements, no filter is required because in the channel, due to the absence of glass, no interfering inelastic scatterings occur.

Preferably, at least the light from the light source is guided to the sample through the channel in the capillary. In the prior art, inelastic scattering of this light in the light guide is the chief source of disturbances. By guiding at least this light through the channel, a narrow band pass filter becomes superfluous. Preferably, however, both light transports, from and to the sample, are guided through the channel. Hence, automatically, there is a complete overlap between the area of the sample which is irradiated and the area from which light returns to the analysis unit. Moreover, thus, for sensitive measurements, no filters are required at the distal end of the light guide, so that the construction remains very simple.

Moreover, when filters can be dispensed with, use of the probe is not limited to a particular wavelength. Ultimate miniaturisation of Raman probes is possible when only one light guide needs to be utilized for supply and discharge of light to and from the sample.

For manufacturing the hollow light guide according to this principle, different techniques can be used. A smooth metal coating can be applied on the inside of a capillary, optionally with a dielectric coating thereon to enhance the resection. Also, an accumulation of dielectric layers can be used, which, together, form a dielectric mirror with a high reflection efficiency. Further, a hollow metal capillary can be utilized, whose inside wall is smooth to such an extent that specular reflection is ensured.

In one embodiment, a capillary is filled with a liquid of a higher refractive index than the material of which the capillary is made, so that for light in the liquid propagating in a certain solid angle through the capillary, total internal reflection occurs at the liquid-capillary transition and the arrangement functions as an optical waveguide. The liquid in the present invention is preferably confined in the capillary, at least at the distal end (adjacent the sample), so that it cannot be easily replaced without opening the capillary. Preferably, the liquid is selected such that it exhibits no significant Raman scattering in the spectral region relevant to the analysis of the sample. This in contrast with optical glass fibres which in large parts of the spectrum cause a continuous high, often broadband signal background. Further, a coating of low refractive index can be applied to the inside of the capillary, thus enabling total internal reflection.

It should be noted here that measuring Raman scattering on liquids in a capillary is known per se. This involves scattering on the liquid in the capillary and not on a sample located beyond the extremity of the capillary. In this known measurement on the liquid, scattering of light from the capillary on a sample outside the capillary is undesired.

The use of hollow light guides based on this invention as a basis for Raman probes renders the construction of these probes simple and increases the possibilities for simple adaptation of probes to application-specific requirements, with regard to the light source to be used and properties of the sample to be examined as well as with regard to spatial resolution and location of the measured volume, by using specific optical elements at the distal extremity of the Raman probe.

An example of such provisions is a cone at the extremity of the light guide and tapering towards the sample, which makes it possible to capture light coming from the sample at a very large solid angle, whereupon in the cone, the solid angle is reduced, so that the light can be more readily guided further in the capillary.

BRIEF DESCRIPTION OF THE DRAWINGS

These and other objects and advantages of the spectrometer according to the invention will be further described with reference to the following figures.

DETAILED DESCRIPTION OF THE PREFERRED EMBODIMENTS

Figure 1A:
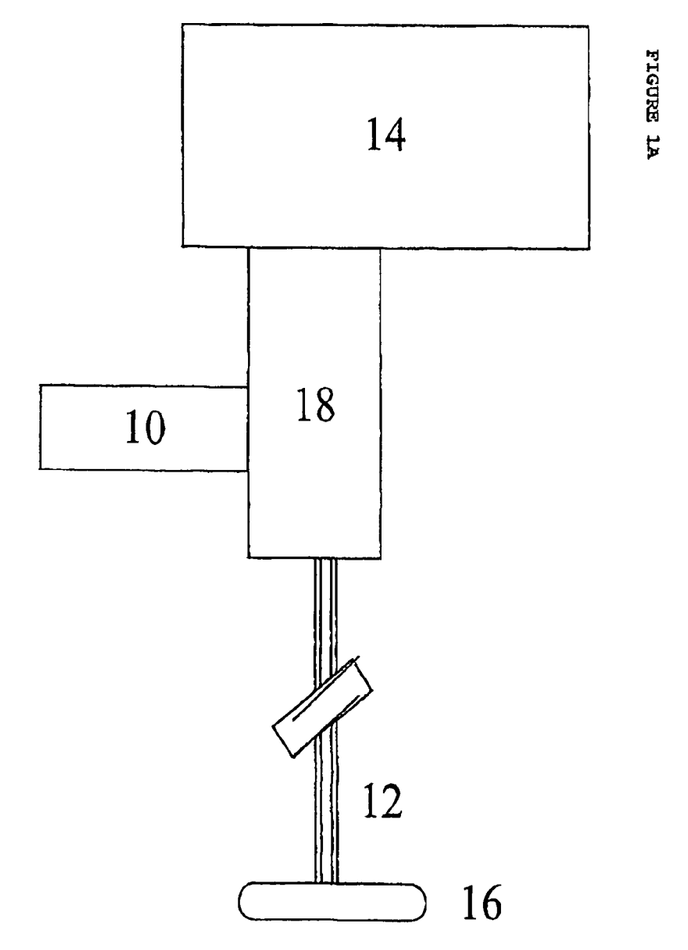
FIG. 1A shows a spectrometer suitable for using Raman probes based on a hollow capillary as light guide.

FIG. 1A shows a sample 16 and a spectrometer for measuring scattering on the sample 16. The spectrometer includes a light source 10, a probe with a hollow capillary 12, an analysis unit 14 and a coupling unit 18 which provides the coupling between the light source 10 and the light guide 12 on the one hand and between wave guide 12 and analysis unit 14 on the other hand.

In operation, with the light source 10, essentially monochromatic light is generated, which is guided via the coupling unit into the hollow light guide 12. This light is guided through the hollow light guide 12 to the sample 16. Light that has been scattered by the sample is guided through the probe, preferably through the hollow light guide, to the analysis unit. In the analysis unit 14, the intensity distribution of the light scattered by the sample 16 is measured as a function of the wavelength. Preferably, measurements are carried out on scattered light whose frequency is shifted by scattering with a shift expressed in inverted centimeters between −4000 and +4000.

Optionally, the polarisation of the scattered light is measured. Optionally, only the intensity and/or polarisation of the scattered light in one or several selected subregions of the spectrum is/are measured. Optionally, the coupling unit 18 can be connected via optical light guides (not shown) to light source 10 and analysis unit 14, respectively.

Figure 1B:
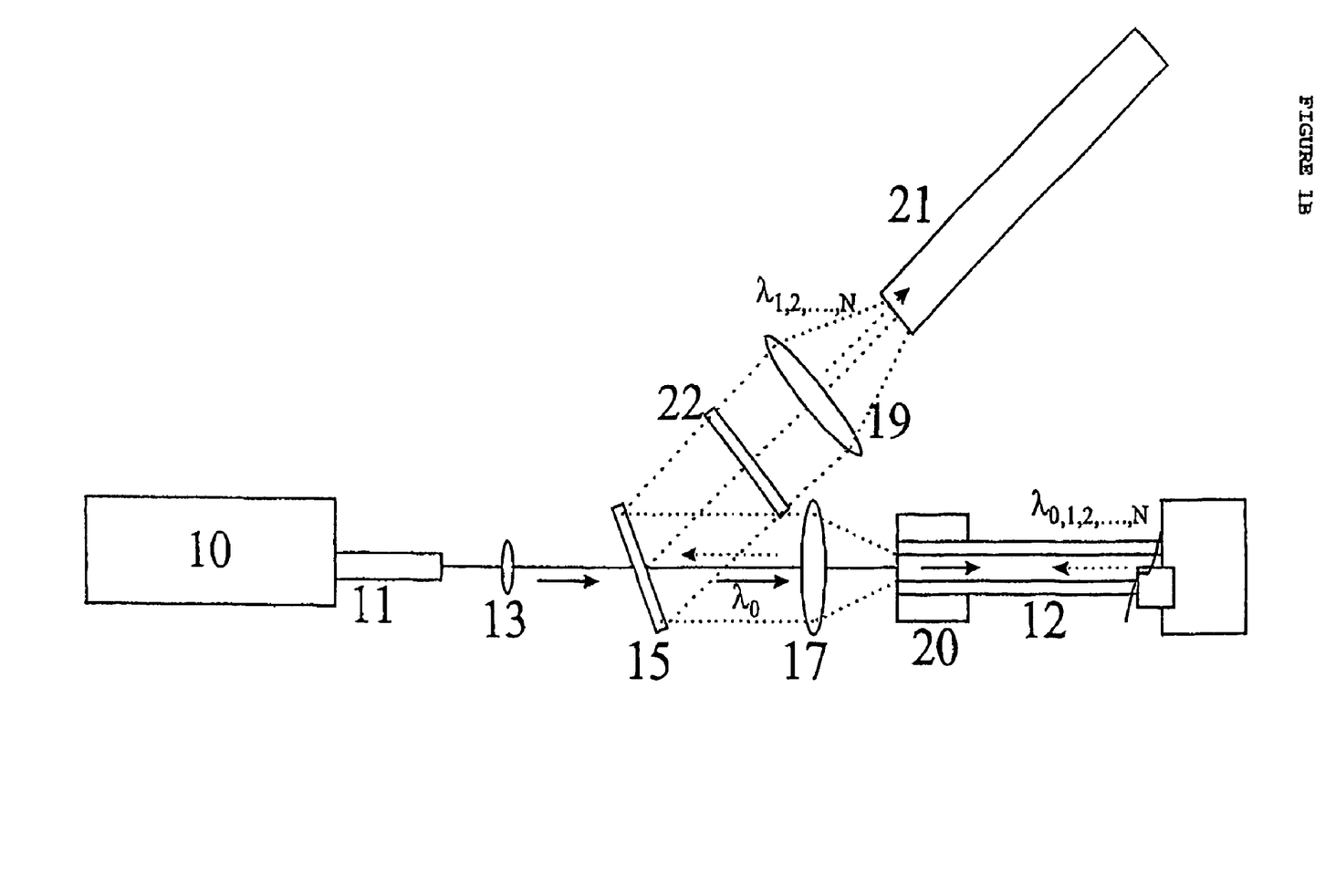
FIG. 1B shows a coupling unit for light source, Raman probe and analysis unit.

FIG. 1B shows a possible embodiment of the coupling unit 18. Light from the light source 10 (represented in full line), preferably a narrow band laser which emits light of a wavelength lo, is coupled-in in an optic fibre 11, preferably a fibre with a small numerical aperture, for instance a monomode fibre. Light issuing at the distal end of this fibre is collimated with the aid of a lens 13 and filtered by a filter 15 so that only the narrow band laser light $l_0$ is coupled-in with the aid of lens 17 into the hollow light guide 12 and reaches the sample. The hollow light guide 12 is attached to coupling unit 14 by means of a mechanic coupling 20, for instance by means of an SMA-coupling or an FC-coupling, so that simply and at will, different light guides can be attached to coupling unit 14, or be exchanged. Light which is scattered by the sample (represented in broken lines) is guided back through the hollow light guide 12 to the coupling unit 18. After collimation by lens 17, this scattered light issuing from the hollow light guide 12 reaches filter 15. Light $l_0$ not shifted in wavelength is largely transmitted through the filter, preferably by more than 99%. Raman scattered light with wavelengths $l_{0,2...N}$ is largely reflected by filter 15, preferably by more than 99%. Filter 22 provides for further suppression of the component lo, whereupon the Raman scattered light is focussed by lens 19 onto a bundle of optic fibres 21. This bundle is for instance circular on the side where the Raman scattered light is focussed, but different shapes are possible. Preferably, the bundle is designed such that as much light as possible is coupled into the core of the fibres of which the bundle consists. The fibres can be circular, square or otherwise multiangular. At the distal side, on which side the light is coupled into the analysis unit 14, the fibres of fibre bundle 21 are arranged in a straight row, perpendicular to the dispersion direction of a dispersive spectrometer.

In this embodiment, the coupling unit 14 is suitable for coupling the hollow light guide 12 to a dispersive analysis unit, in which the width dimension of the row of fibres is partly determinative of the spectral resolution of the device. This is not the case when the analysis unit 14 is a Fourier-Transform Raman spectrometer or when, with the aid of optic fibres, the intensity of the scattered light is measured ill only one or several wavelength intervals. In these two cases, fibre bundle 21 can be optionally omitted.

In a different embodiment of the coupling unit, filter 15 is replaced with a mirror which reflects the light issuing from the hollow light guide in the direction of filter 22. The light from light source 10 reaches the hollow light guide through a hole in the mirror of a diameter which is relatively small with regard to the total mirror surface.

In a different embodiment (not shown) laser light is coupled into the hollow light guide via a small mirror. The surface of the mirror is small with respect to the diameter of the light beam issuing from the hollow light guide and collimated by a lens. In still another embodiment (not shown) laser light is coupled into the hollow light guide via a small mirror placed between a lens and the hollow light guide.

Figure 2:
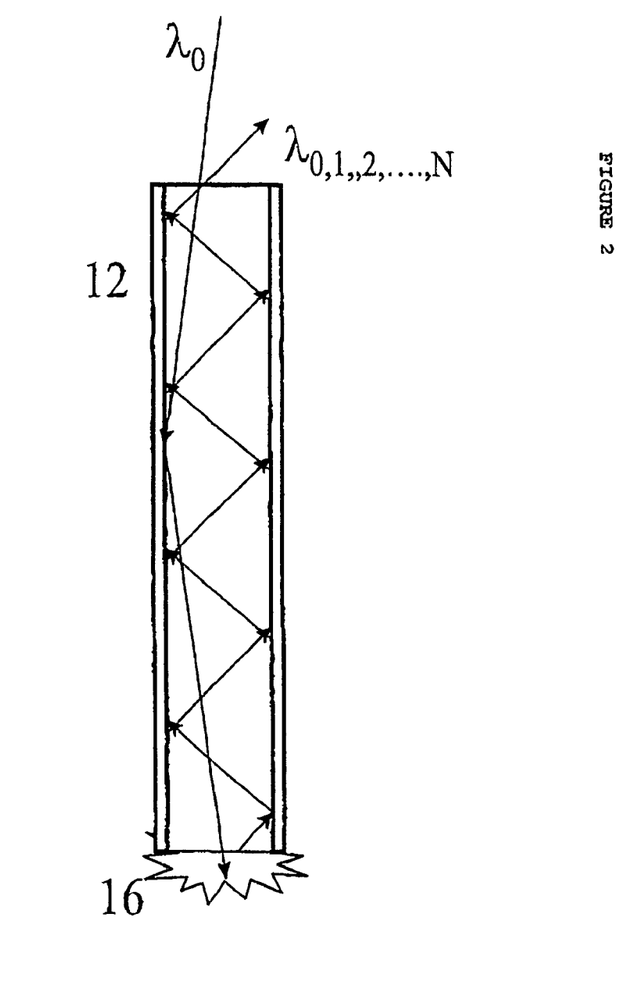
FIG. 2 shows the principle of the use for Raman spectroscopy of a probe based on a capillary.

FIG. 2 shows the principle of the use of a capillary 12 as hollow light guide for Raman spectroscopy light of wavelength $l_0$ from light source 10 (not shown) is coupled in via coupling unit 18 (not shown) in capillary 12 and is reflected on the inner wall of the capillary and reaches the sample 16. The sample scatters the incident light through elastic and inelastic scattering. A portion of this scattered light, consisting of a strong component of, a wavelength $l_0$ and, in addition, components $l_{1,2,...,N}$ shifted in wavelengths, is intercepted by capillary 12 and guided back to the coupling unit 14 (not shown) to which capillary 12 is connected by means of a mechanical coupling 20 (not shown).

Figure 3A:
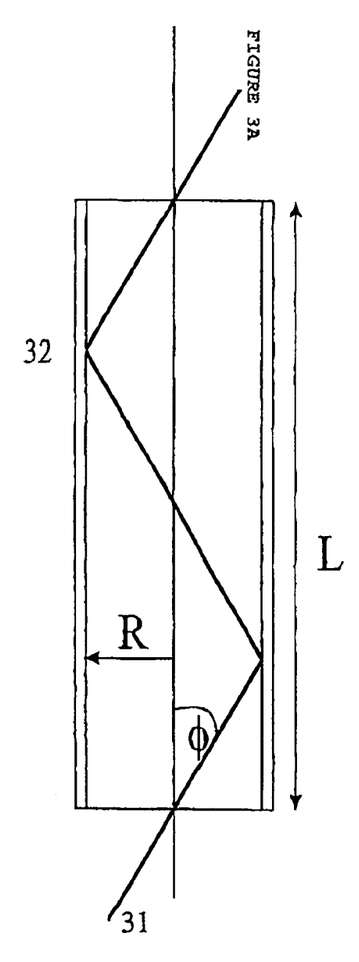
FIGS. 3A–3C show different embodiments of a light guide suitable for Raman spectroscopy.
Figure 3B:
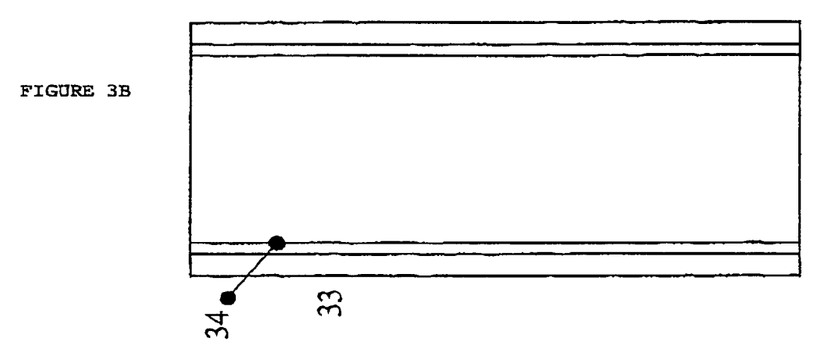
Figure 3C:
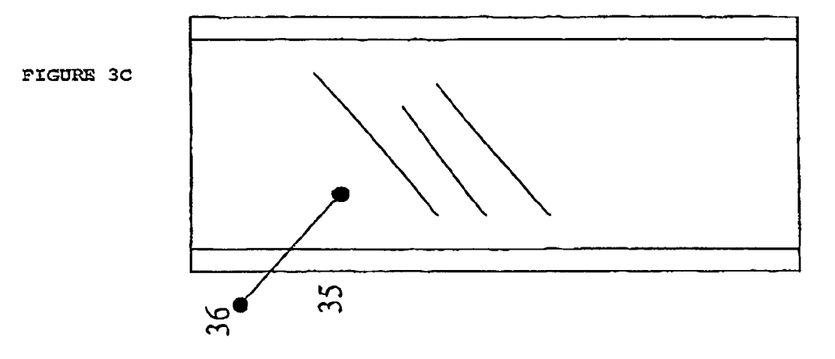

FIGS. 3A–C shows different possible embodiments of the hollow light guide.

FIG. 3A shows a capillary 32 made of a material having an intrinsically high reflection coefficient for the relevant part of the electromagnetic spectrum, for instance of metal. The inside of the capillary is sufficiently flat, so that specular reflection from the walls dominates. Gold has a high reflection in the near-infrared (>800 nm) of 98–99%. For applications in the ultraviolet, aluminum is preferred. When the length of the hollow light guide remains limited, such a capillary suffices for the application described here. In a longer capillary, the reflection losses could become a drawback when signal is intercepted from a sample which inherently emits a weak signal. For a light ray 31, entering through the centre of the capillary 32 at an angle φ to the axis of the capillary, having a radius R and a length L, and made of a material having reflection coefficient ρ, the weakening as a result of reflection losses can be assessed with the aid of formula 1.

$$I_{out}/I_{in} \approx \rho^{L \tan \phi / 2R} \quad (1)$$

For a gold capillary of a diameter of 1 mm and a length of 50 cm and light incidence at an angle φ of maximally 6°, this reflection loss is then approximately 64%.

FIG. 3B shows a capillary made of fused silica, glass or a plastic 33, whose inner wall is provided with a reflecting metal coating 34. For the metal, in these embodiments, aluminum (particularly suitable for use in the ultraviolet), silver (for use with visible light and in the near-infrared) or gold (near-infrared) can be utilized. The inside has been smoothed such that specular reflection occurs. In a further embodiment a dielectric layer can be applied on the reflecting layer to increase the reflection coefficient. Light guides according to this principle are known per se which exhibit a transmission of approximately. 90%/m. Such light guides are suitable in particular for applications where the light guide does not need to be bent or hardly so. Sharp bends lead to strong decrease of the transmission.

Further, on the inner wall of the capillary, an accumulation of dielectric layers can be applied, selected such that in the spectral region of interest an optimum reflection is accomplished at every angle of incidence. Such a hollow light guide, whose walls function as so-called omni-directional reflector is, described in Fink, Y. et al J. Lightwave Technology 17:2039–2041 (1999).

FIG. 3C shows a capillary 35 non-absorbing in the relevant spectral region and transparent, filled will liquid 36 non-absorbing in the relevant spectral region, having no Raman signal in the spectral regions of interest to the user. The light guide with liquid is based on the principle of total internal reflection with which very high transmission-efficiency can be attained, which is moreover little influenced by bends in the light guide. This means that the refractive index of the liquid needs to be higher than that of the capillary material. The numerical aperture of this light guide is determined by formula 2:

$$N.A. = \sqrt{(n_1^2 - n_2^2)} \quad (2)$$

A possible option for liquid 36 is tetrachloroethylene. Use of this agent having a refractive index of ~15.05 and only Raman scattering at ~1571 cm–1 and below 525 cm–1 leaves a large part of the Raman spectrum free for measurements on a sample. When a fused silica (refractive index ~1.46) capillary is filled with this liquid, a light guide is formed with a numerical aperture of –0.36. Another possible choice is CC14. It will be clear that, depending on the application (i.e. depending, inter alia, on which part or which parts of the spectrum have to be clear of background signal contributions of the Raman probe) a particular liquid can be chosen, and that there is a large freedom in that respect.

It will be clear that many other variations on the above-mentioned examples are possible, such as, for instance, a capillary filled with a liquid of a lower refractive index than the material of which the capillary is made. The principle of light guidance through total internal reflection can then be realized by employing a coating of the inside wall of the capillary with a material having a refractive index lower than the refractive index of the liquid.

In principle, it is also possible to guide light through the capillary by using total internal reflection on the transition of capillary material and air at the outer side of the capillary. However, this is a less advantageous solution. On the one hand, also a portion of the Raman signal generated in the capillary material will be guided into the light guide. On the other hand, total internal reflection will (can) be lost at locations where the outside of the capillary is in contact with other materials.

To obviate this last-mentioned problem, a coating of a material with a lower refractive index than the refractive index of the liquid can be applied on the outside of the capillary. The disadvantage remains that a portion of the Raman signal generated in the capillary material is transmitted into the liquid core. Onto the coating on the outside of the capillary a strongly absorbing coating has to be applied because, otherwise, total internal reflection on the transition of coating and air occurs.

In the embodiments of FIGS. 2 and 3, the Raman capillary is simply * cut off at the exit. In the case of a light guide with a liquid core as described, a transparent sealing of the capillary will be used at both ends. In this case, the choice of diameter of the capillary determines the magnitude of the measured surface and/or of the measured volume in the sample of which scattered light is captured.

Other embodiments of the extremity are possible. The shape of the extremity of the Raman capillary, i.e. the side of the hollow light guide where the sample is located, can be varied. This makes it possible, for instance, to use the Raman capillary for illumination of a sample and/or signal collection from a sample at an angle or angles deviating from the direction of the longitudinal axis of the capillary and/or are not centered about the longitudinal axis of the Raman capillary. It can also be provided that control is obtained over the location of the measured volume from which preferentially light is intercepted and/or the spatial resolution of the Raman capillary. It can also be provided that light scattered by the sample can be intercepted within a large solid angle, whereupon this solid angle is transformed to a smaller solid angle which can be (efficiently) guided through the capillary. A number of examples are discussed in FIGS. 4 to 8.

Figure 4:
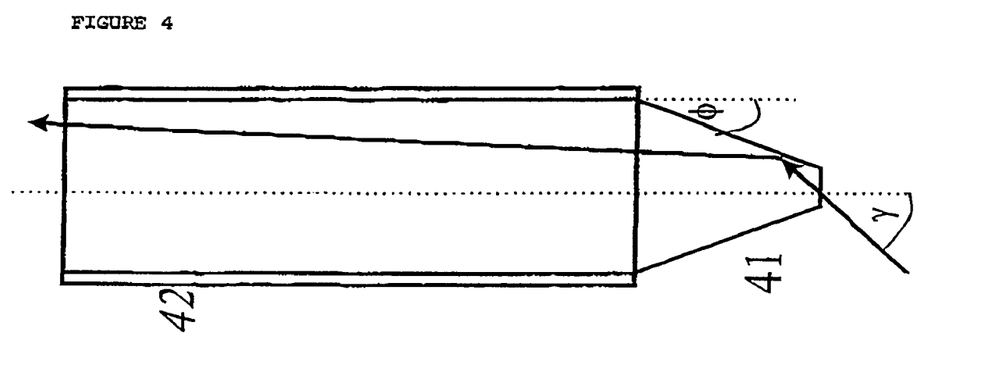
FIGS. 4–8 show different embodiments of Raman probes based on light conducting capillaries.

FIG. 4 shows an embodiment of the light guide with an element 41 at the distal end (the part of the probe which is in contact with the sample) which brings about a solid angle adaptation. The element 41 is for instance manufactured from a material which gives off no or only a relatively weak Raman signal in the relevant part of the Raman spectrum. An example of such a material is UV-grade $CaF_2$, as can be supplied by, for instance, the firm Crystran Ltd, 27 Factory Road, Poole, Dorset BH16 5SL, United Kingdom.

The element 41 is for instance cone-shaped. The sides of the element make an angle $\phi$ with the longitudinal a of the Raman capillary 42. When light is intercepted by element 41 at an angle $\gamma$, larger than $\phi$, with the longitudinal axis of the capillary, then, after reflection from the wall of element 41, the light will travel further at an angle $\gamma'$ with the longitudinal axis of the capillary which is smaller than the original angle of incidence $\gamma$. When angle $\gamma$ is large, more reflections with the sides of element 41 can occur before the light proceeds in the Raman capillary 42. Many variations on the shape of element 41 with a view to adjusting the solid angle at which intercepted signal is guided further, are possible. For Raman capillaries in which use is made of a reflecting coating on the inside wall of capillary, this has the great advantage that this limits the number of reflections of the intercepted Raman light against the walls of the hollow light guide en route to the detector, and hence also reflection losses. For Raman capillaries in which use is made of total internal reflection, this has the advantage that signal from the sample can be intercepted at a larger solid angle than could be guided further by the Raman capillary.

Also at the detector side of the hollow light guide such a cone or an optimized non-imaging parabolic light collector can be attached. There, it serves as a numerical aperture adapter, for the analysis unit.

Figure 5:
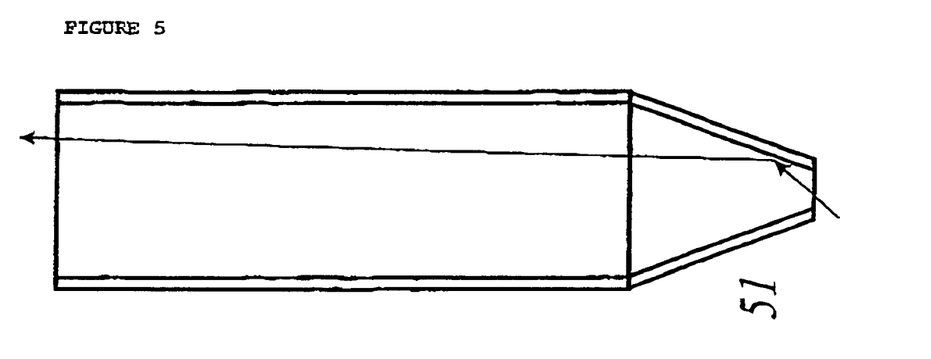

FIG. 5 shows a light guide with a tapering hollow element 51 with a reflecting wall at the distal end which effects a similar sort of solid angle adjustment to element 41 in FIG. 4.

Figure 6:
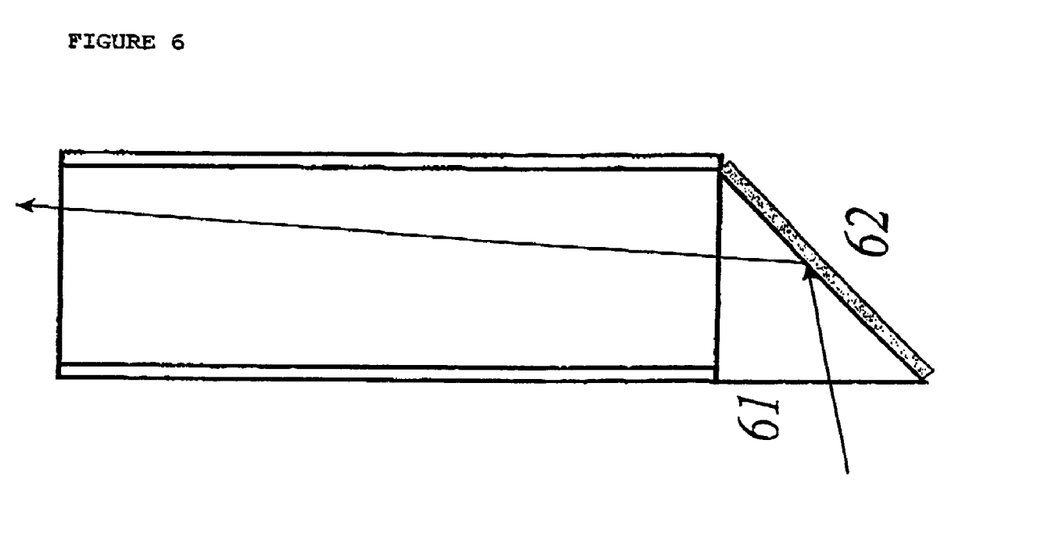

FIG. 6 shows a light guide with a reflecting element 61 at the distal end having for an object to make the light guide view sideways. This reflecting element can for instance be a microprism with a reflecting layer 62 applied thereon. Various other embodiments are possible.

Figure 7:
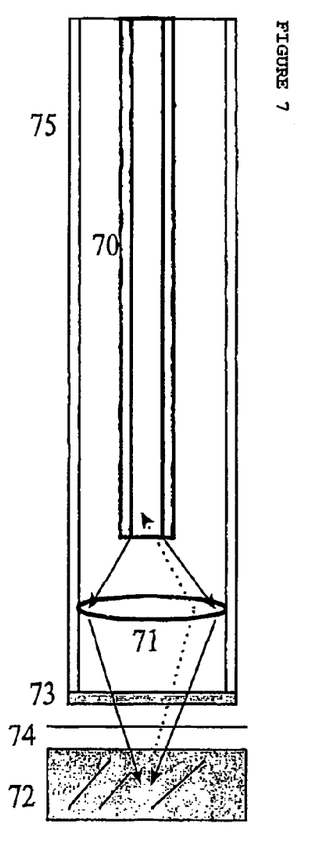

FIG. 7 shows a capillary 70 whose extremity is depicted through a lens 71 in a volume of the sample 72 or on a surface of the sample 72. In particular the light which is scattered in the same volume of the sample or on the same part of the surface of the sample is, again, coupled-in with great efficiency in capillary 70. In this way, in a simple manner, a confocal measurement arrangement is created with which accurate control is obtained over which part of the sample is examined. The choice of the lens and capillary deter together determine the spatial resolution of a probe in this embodiment. Also, this renders it possible to place an extra window 73 at the extremity of the Raman probe, which falls outside the measured volume of the probe, and therefore does not cause an interfering Raman signal background. For the same reason, with such a probe, it becomes possible to measure a sample through a transparent container wall 74 without measuring an interfering Raman signal from the wall material. The housing 75 of this embodiment can be adapted to the specific application.

Figure 8:
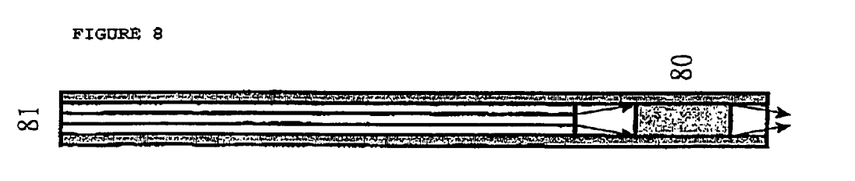

FIG. 8 shows an embodiment as in FIG. 7 in which the lens is replaced by a gradient index lens 80. Lens and core diameter of capillary 81 together are determinative of the spatial resolution.

Figure 9:
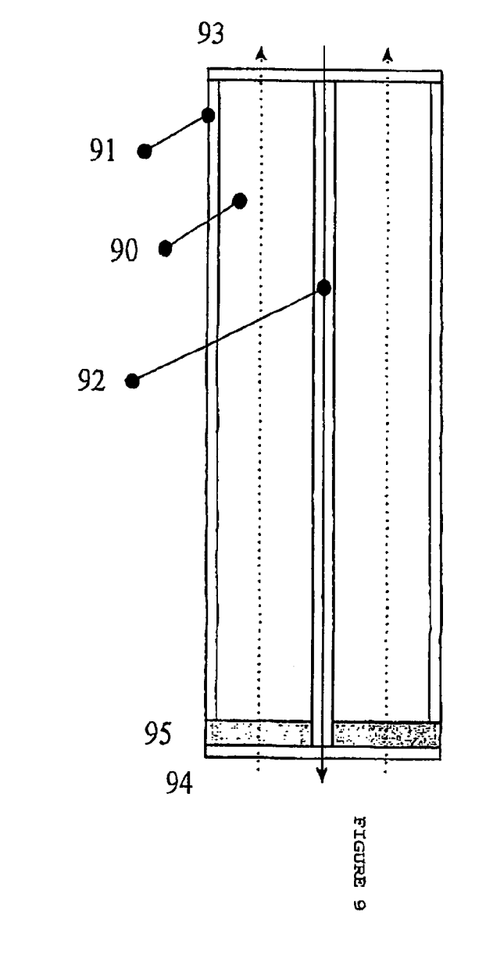
FIGS. 9–13 show different embodiments of Raman probes based on thick-walled capillaries.

FIG. 9 shows the use of a thick-walled capillary 90 as a guide for light to and from a sample to be examined. On the outside, the capillary is coated with a material 91 of lower refractive index than the material of the capillary, while the layer thickness of this coating is sufficiently great for the effects on the interface between capillary material and coating to be determined by the bulk properties of the coating material. The capillary is filled with a liquid 92 of a higher refractive index than the material of which the capillary is made. Light from light source 10 (not shown) is introduced into the capillary within a solid angle which is smaller than the maximum solid angle at which the liquid core can guide light (given by formula 2). Further, the liquid 92 is selected such that in the spectral region relevant to the measurement, no significantly interfering overlap occurs between the scattering spectrum of the sample and the scattering spectrum of the liquid. Through this suitable choice of liquid and wall material, a light guide is created through which light from light source 10 (not shown) can be guided to the sample to be examined. Light scattered by the sample can be guided back through the wall of the capillary to the analysis unit 14 (not shown), via a Coupling unit 18 (not shown). At the top and bottom, the capillary is closed off with the aid of thin transparent windows 93, 94. If the Raman spectrum of the capillary material overlaps the spectrum of the sample to be examined in a significantly interfering manner, a filter 95 can be provided on the capillary on the side of the sample, which filter screens light elastically scattered by the sample. Accordingly, this prevents an interfering Raman signal being generated in the wall of the capillary. Eligible for serving as a substrate for the filter is a thin, smoothly polished disk sawn off from the capillary having the same dimensions. Such a filter can then be positioned and fastened onto the capillary in a simple manner; The refractive indices of liquid and capillary material determine the solid angle at which light from light source 10 (not shown) can be coupled-in into the light guide and at which the sample can be illuminated, according to formula 2 for the numerical aperture of a light guide.

In the same manner, the solid angle at which light scattered by the sample can be intercepted and guided further to the coupling unit 18 (not shown) is determined by the refractive indices of the capillary material and the coating on the outside of the capillary.

In an alternative embodiment, the capillary is coated on the outside with a highly reflective material, preferably a gold or silver coating or an omni-directionally reflecting dielectric coating. Optionally, depending on the application, a coating can be dispensed with, so that total internal reflection can occur at the transition of capillary and air.

In a different embodiment, conversely, the excitation light is guided through the wall of the capillary to the sample, with optional filtering at the extremity of the capillary, and light scattered by the sample is guided via a channel of the capillary to the analysis unit.

Figure 10:
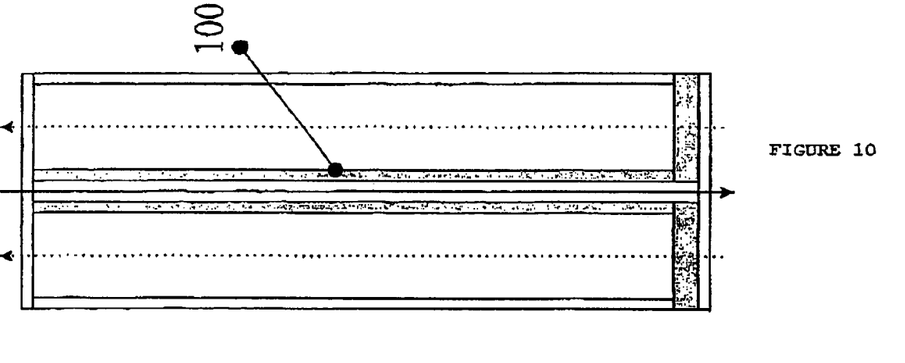

FIG. 10 shows a further embodiment, in which the capillary is not filled with a liquid but in which the inside wall of the capillary has been made strongly reflective, for instance through application of a silver layer and a dielectric layer 100.

Figure 11:
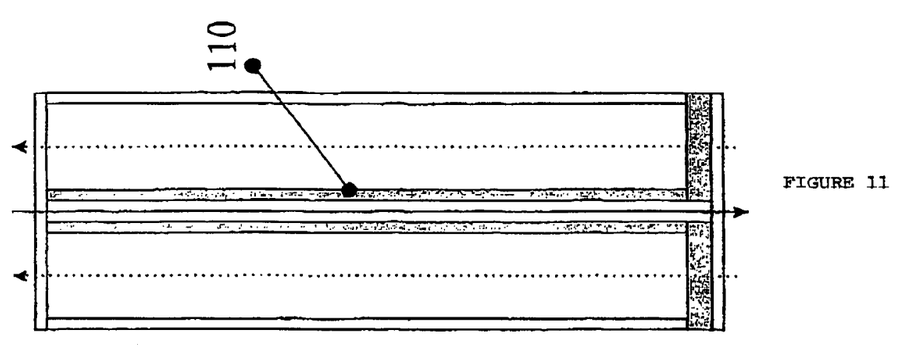

FIG. 11 shows a further embodiment in which the inside of the capillary is coated with a material 110 of lower refractive index than both the liquid in the core of the capillary and the material of the capillary. In this manner, the liquid core of the Raman capillary through which light from the light source 10 (not shown) is guided to the sample and the wall of the capillary through which light Raman scattered by the sample is discharged to the analysis unit 18 (not shown) are optically separated from each other.

Figure 12:
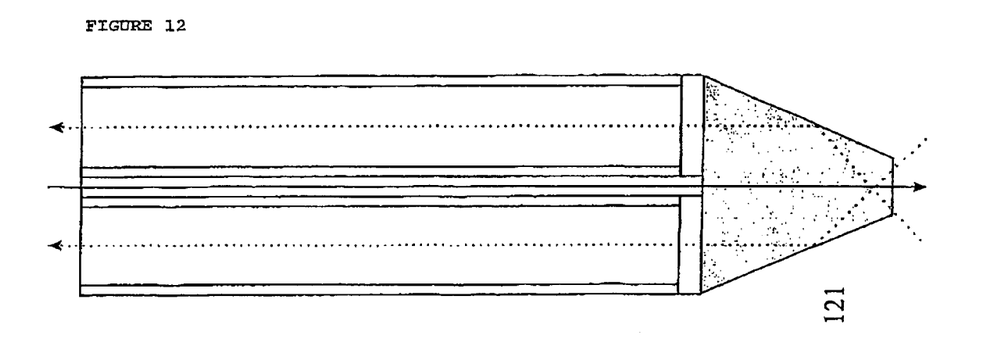

FIG. 12 shows a further embodiment, in which the capillary according to FIG. 9, 10 or 11 is provided with an element 121 on the side where the sample to be examined is located. Use of this element provides for optimal overlap between irradiated sample-volume and sample-volume from which light is intercepted. Further, the element serves for conversion of the large solid angle at which light scattered by the sample is intercepted, to a smaller solid angle, which light can be guided back through the capillary in the direction of the analysis unit 18 (not shown). The element has, for instance, the shape of a cone, but other shapes are also possible. Preferably, the element is manufactured from a material which does not emit a significantly interfering Raman signal in the relevant spectral range. For several applications, for instance UV-grade calcium fluoride is a good option, because this material has a strong Raman band only at 312 cm−1. The element can be coated with a strongly reflecting coating, for instance gold, or with a material of lower refractive index so that total internal reflection occurs. A suitable choice is, for instance, Teflon AF (produced by DuPont) having a refractive index of 1.29–1.31.

Figure 13:
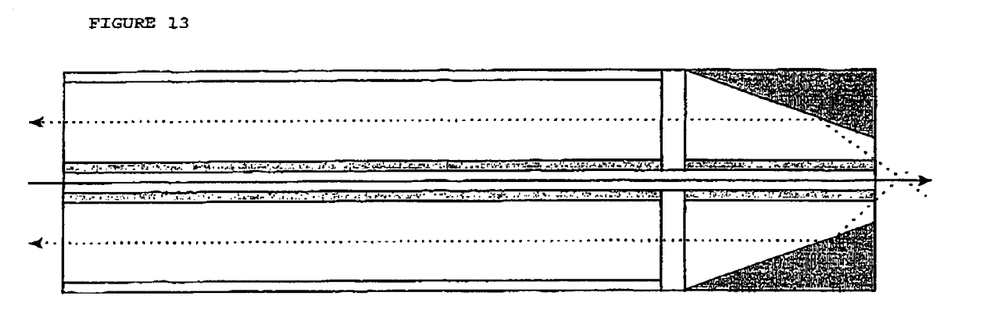

FIG. 13 shows a further embodiment in which the capillary according to FIG. 10 or 11 is provided with an element 131 as in FIG. 12, but for which a 10 same capillary as of which the light guide is made serves as base material, which is subsequently brought into the desired shape by grinding and polishing or in a different mater. This offers advantages in view of a simpler manner of production, which can be utilized if the Raman signal background of the capillary material which is generated in the element does not have a significantly interfering effect. Additionally, this embodiment offers the possibility of displacement of the measured volume to a location deeper into the sample, since signal does not necessarily need to be intercepted directly from the surface of the sample (for instance when the inside of the element is coated with a reflecting metal layer).

Figure 14:
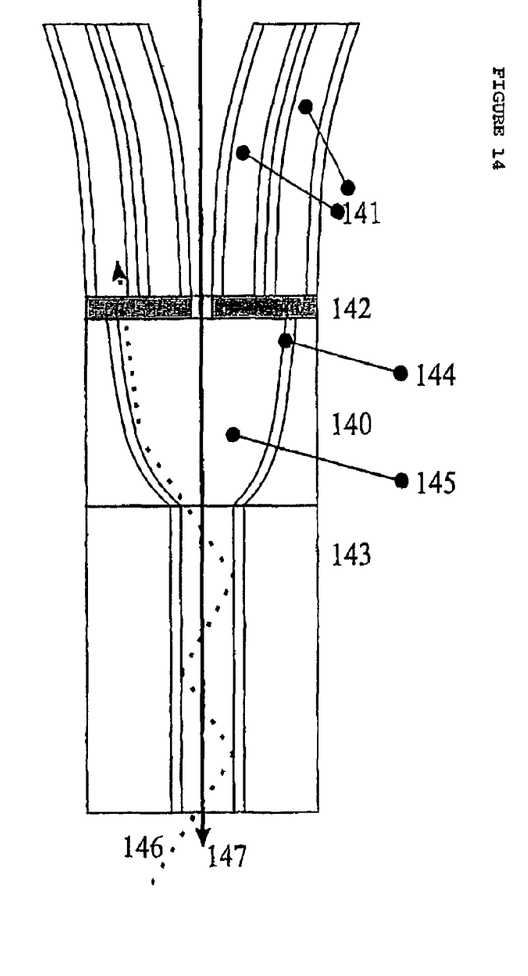
FIG. 14 shows an alternative embodiment of a coupling unit for light source, Raman probe and analysis unit.

FIG. 14 shows an alternative embodiment of coupling unit 18. The extremity of the light guide 12 is coupled to an element 140 which reduces the solid angle at which light 146 issues from the hollow light guide, which enables this light being coupled-in and guided further with the aid of standard optic glass fibres 141 with, for instance, a numerical aperture of 0.22. A filter 142 serves for blocking light of the same wavelength as the light from light source 10 (not shown). Through a relatively saw hole in the filter, light 147 is coupled in from light source 10 (not shown) in capillary 143. This capillary can have one of the embodiments as described hereinabove or derived therefrom. Elements 140 can for instance be manufactured by taking as a basis so-called fibre optic ferrules, as sold, for instance, by Vitrocom (Mountain Lakes, N.J., USA). The inside wall is made strongly reflective, for instance by applying a gold or silver coating 144.

In an alternative embodiment, element 140 is filled with a liquid 145 of a higher refractive index than the wall material of element 140, so that total internal reflection occurs at the transition between liquid and wall material.

The invention claimed is:

1. A spectrometer for measuring inelastically scattered light, provided with
    a light source;
    an analysis unit for analysis of a spectral distribution of light from the light source which has been scattered by a sample;
    a probe provided with a capillary through which light from the light source is guided to the sample and scattered light is guided from the sample to the analysis unit, wherein the capillary comprises a wall and a channel, so that for light at a transition from the channel to the wall internal reflection occurs, wherein the capillary is connected such that the channel transports light from the light source and/or the scattered light which is guided to the analysis unit.

2. A spectrometer according to claim 1, wherein at least virtually all the light from the light source which is guided to the sample is guided through the channel.

3. A spectrometer according to claim 2, wherein also at least virtually all the scattered light is guided through the channel.

4. A spectrometer according to claim 1, wherein at an extremity of the capillary on a side of the sample, provisions are made for manipulating a spatial distribution of the light which is guided from or to the sample via the exit.

5. A spectrometer according to claim 1, wherein the channel is filled with a liquid of higher refractive index than the wall of the capillary.

6. A spectrometer according to claim 1, wherein between the wall and the channel a mirroring metal coating is applied.

7. A spectrometer according to claim 6, wherein a dielectric coating is applied to the metal coating.

8. A spectrometer according to claim 1, wherein between the wall and the channel, an accumulation of dielectric layers is provided which act in a reflecting manner in the spectral operating range of the spectrometer.

9. A spectrometer according to claim 1, wherein a first boundary surface of the wall and/or a second boundary surface of the wall with an environment are coated with a material of a refractive index smaller than that of the wall between the boundary surfaces and/or, if the channel is filled with a liquid, smaller than that of the liquid.

10. A probe for use in a Raman spectrometer, provided with
    a first connection for a light source and an analysis unit,
    a second connection for illuminating a sample to be examined with the light of the light source and intercepting scattered light from the sample,
    a light guide for guiding light between the connections, wherein the light guide comprises a capillary with a channel and a wall, so that for light at a transition of the channel to the wall, internal reflection occurs, wherein the capillary is connected to the connection such that the channel transports light between the connections in at least one direction.

11. A probe according to claim 10, wherein at least virtually all the light of the light source which is guided to the sample is guided through the channel.

12. A probe according to claim 11, wherein also at least virtually all the scattered light is guided through the channel.

13. A probe according to claim 10, wherein at an extremity of the light guide on a side of the exit provisions are made for manipulating a spatial distribution of the light which is guided from or to a sample via the exit.

14. A probe according to claim 10, wherein the channel is filled with a liquid of higher refractive index than the wall of the capillary.

15. A probe according to claim 10, wherein between the wall and the channel is a mirroring metal coating is applied.

16. A probe according to claim 10, wherein a dielectric coating is applied on the metal coating.

17. A probe according to claim 10, wherein between the wall and the channel an accumulation of dielectric layer is provided which act in a reflecting manner in the spectral operating range of the spectrometer.

18. A probe according to claim 10, wherein a first boundary surface of the wall and/or a second boundary surface of the wall with an environment are coated with a material of refractive index smaller than that of the wall between the boundary surfaces and/or, if the channel is filled with a liquid, smaller than that of the liquid.

19. A method for measuring a spectrum of light inelastically scattered by a sample, wherein both light from a light source to be scattered and scattered light are guided through a capillary, respectively from a light source to a sample and from the sample to an analysis unit, which capillary is designed such that for light from the light source on a transition of a channel in the capillary and a wall of the capillary reflection occurs during guidance of the light from the light source to the sample, wherein the light to be scattered and/or the scattered light is guided through the channel.

20. A method according to claim 19, wherein the light to be scattered is guided through the channel.

21. A method according to claim 19, wherein both the light to be scattered and the scattered light are guided through the channel.

22. A method according to claim 19, wherein the channel is filled with a liquid.

* * * * *